United States Patent [19]
Perkins

[11] Patent Number: 5,189,449
[45] Date of Patent: Feb. 23, 1993

[54] RETINOSCOPE WITH EXTERNAL CONTROL SLEEVE

[75] Inventor: David G. Perkins, Syracuse, N.Y.

[73] Assignee: Welch Allyn, Inc., Skaneateles Falls, N.Y.

[21] Appl. No.: 757,897

[22] Filed: Sep. 11, 1991

[51] Int. Cl.$^5$ ............................................. A61B 3/10
[52] U.S. Cl. .................... 351/211; 351/205; 351/213
[58] Field of Search ............... 351/205, 211, 213, 215, 351/218

[56] References Cited

U.S. PATENT DOCUMENTS 2,501,438  3/1951  Copeland .......................... 351/211
3,439,978  4/1969  Moore et al. ...................... 351/205

Primary Examiner—Bruce Y. Arnold
Assistant Examiner—Hung Xuan Dang
Attorney, Agent, or Firm—Wall and Roehrig

[57] ABSTRACT

A streak retinoscope has an external control sleeve that is fully rotatable and is movable axially for rotating the lamp and focusing the lens assembly, respectively. The lens assembly is carried on the lens holder and the lamp assembly is carried on a lamp carrier. The lamp carrier is rotatable but is held against axial motion, while the lens holder sleeve is held against rotation but is movable axially. A sliding gear arrangement is formed wherein the lamp carrier sleeve is configured with axially elongated teeth, thus serving as a sun gear. The outer control sleeve has internal teeth and serves as the ring gear. Planet gears can be carried on the lens carrier sleeve.

11 Claims, 4 Drawing Sheets

RETINOSCOPE WITH EXTERNAL CONTROL SLEEVE

BACKGROUND OF THE INVENTION

The present invention relates to hand-held medical diagnostic instruments of the type which contain a light source, and is more particularly concerned with a streak retinoscope in which a bar or streak of light can be focussed and defocussed and continuously adjusted at any angle by use of a control sleeve on the instrument's handle.

Streak retinoscopy provides the eye practitioner with valuable information about the refractive state of a patient's eyes. Streak retinoscopy, in conjunction with trial lenses, can not only measure the refractive error of the eye but can also determine the axis of astigmatism.

In streak retinoscopy, a streak or bar of light, as distinguished from a spot of light, is projected through the lens of the eye onto the retina, and the image of the streak on the retina is observed by the practitioner. For effective examination, the streak or bar should be fully rotatable 360 degrees and beyond without a stop. Full 360 degree rotation is advantageous in that the streak can be rotated from any starting position. The physician or other practitioner should also be afforded freedom in the use of hands, so that the angular and focussing adjustments can be carried out with the right hand alone or with the left hand alone.

A typical retinoscope illustrative of the state of the art is shown and described in U.S. Pat. No. 3,439,978, granted Apr. 22, 1969, and is also shown in U.S. Pat No. Des. 243,973, granted Apr. 5, 1977.

Other hand-held diagnostic instruments having a light source and a power source contained in their handles are shown in U.S. Pat. No. 4,147,163, granted Apr. 3, 1979, and in U.S. Pat. No. 3,441,340, granted Apr. 29, 1969.

The present retinoscopes as described e.g. in U.S. Pat. No. 3,439,978 usually achieve rotation with a control sleeve that is fitted inside an outer sleeve. The outer sleeve has openings or slots that permit the practitioner to rotate the control sleeve using his or her fingers. The control sleeve can also be manipulated up and down within the outer sleeve to move the lens nearer or further from the lamp.

The retinoscope of this system requires adjustment of the angular position of the head to the handle for convenient positioning of the slots in the outer sleeve. This can require loosening and tightening of a separate nut or actually removing the head and adjusting the orientation of the head to slots. Some instruments do not allow adjustment of slot orientation to head. Some retinoscopes have external control sleeves but because of mechanical constraints cannot rotate more than about 180 degrees.

OBJECTS AND SUMMARY OF THE INVENTION

It is a principal object of the present invention to provide an instrument over prior streak retinoscopes.

It is a more specific object to provide a streak retinoscope which can achieve full 360 degree rotational motion and focusing control with a convenient external control sleeve that can easily be actuated with any grip and with same hand holding the power supply handle.

It is another object to provide a retinoscope which requires no adjustment of the retinoscope relative to hand position for right hand use or left hand use.

It is a further object to provide a retinoscope in which the lamp is convenient to remove and install.

According to an aspect of this invention, the streak retinoscope includes a beam splitter mirror joined to the head assembly including a main sleeve assembly which contains the streak lamp and focussing lens for it. In the preferred embodiment, the main sleeve assembly is fitted with a control sleeve that is fully rotatable around the handle and is movable for rotating the lamp and focussing the lens assembly. The lens is carried on a lens holder and the lamp assembly is carried on a lamp carrier. The lamp carrier is rotatable, but held against axial motion, while the lens holder is held against rotation but is movable axially. A planetary gear arrangement can be formed by these sleeves. The lamp carrier has gear teeth on its exterior and serves as a sun gear. The control sleeve has internal teeth and serves as the annulus gear. Planet gears are carried on the lens holder. Axial movement of the control sleeve moves the lens assembly for focussing, and rotation of the control sleeve correspondingly rotates the lamp assembly to control the angular position of the streak of light. The control sleeve can conveniently take the form of a large knurled ring.

Many other objects, features, and advantages of this invention will become apparent from the ensuing description of a preferred embodiment, to be read in conjunction with the appended Drawing.

DETAILED DESCRIPTION OF THE PREFERRED EMBODIMENT

Figures 1, 5:
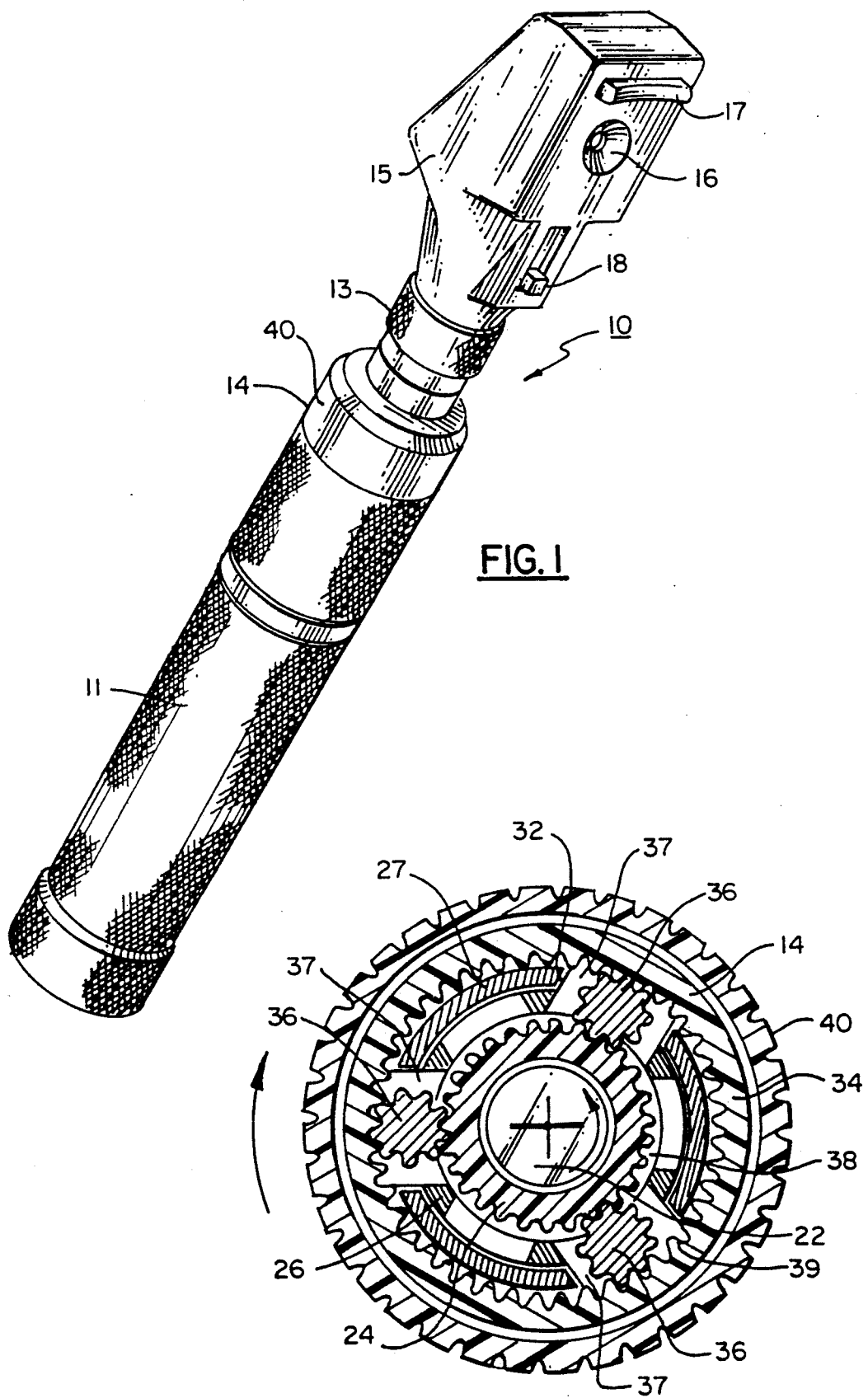
FIG. 1 is a perspective view of a retinoscope according to one embodiment of this invention.
FIG. 5 is a cross sectional view taken at 5—5 of FIG. 3.
Figure 2:
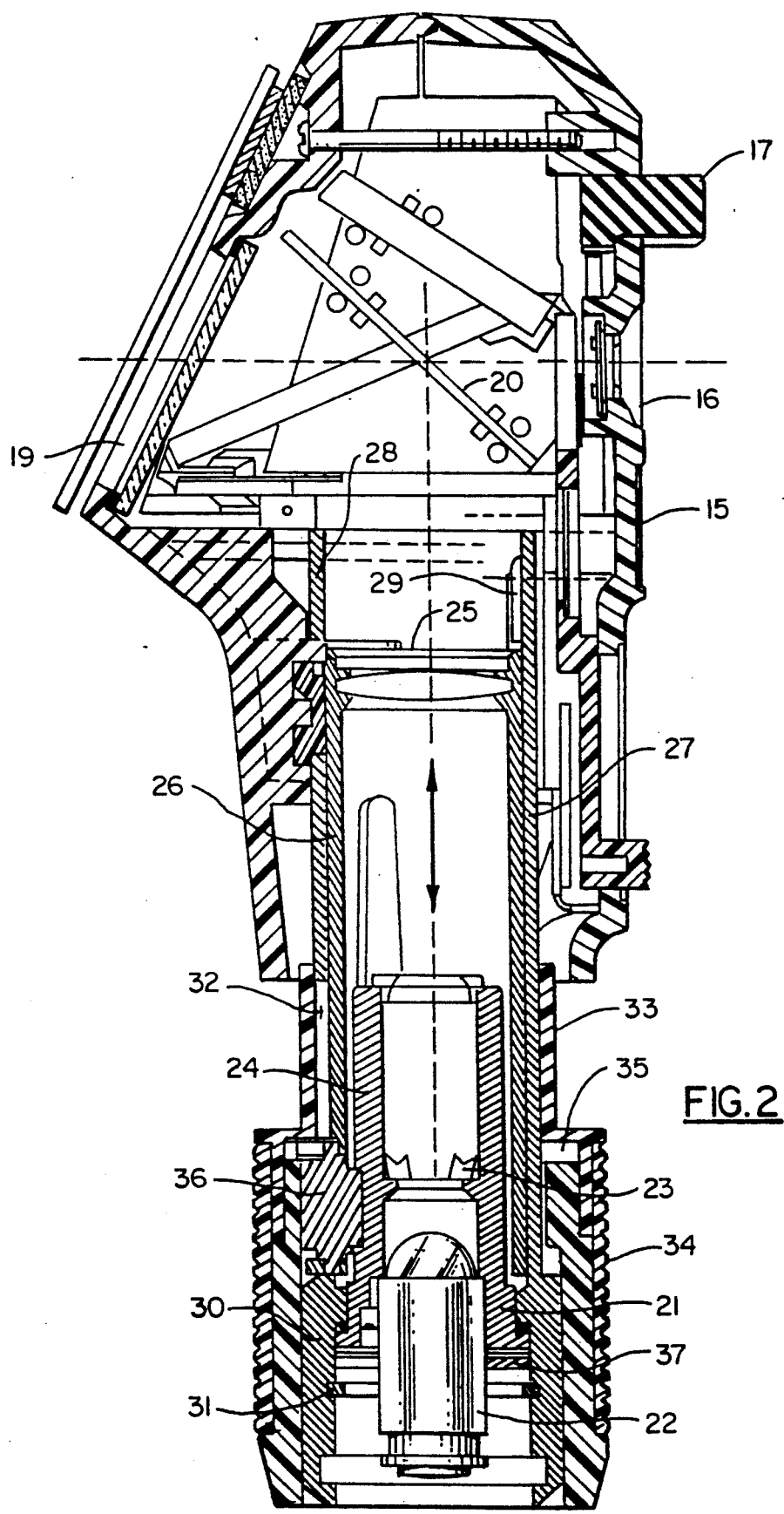
FIG. 2 is a section of the head portion and main sleeve subassembly portion of the retinoscope of a preferred embodiment.

With reference to the Drawing, and initially to FIG. 1, a streak retinoscope 10 according to the present invention has a power handle 11 which includes means coupled to a power source (battery or wall transformer, for example) and a main sleeve subassembly sleeve 13, including an external control sleeve assembly 14. The control sleeve 13 is affixed onto a head portion 15 having a viewing port 16 and brow rest 17 on the doctor's side of the instrument. There is also a switch 18 for controlling a filter. As better shown in FIG. 2, on an opposite or patient side there is a window 19. The head portion 15 contains a beam splitter 20 disposed at approximately a 45 degree angle for reflecting the streak of light from the lamp carrier assembly 21 through the window 19 into the patient's eye, and permitting the streak of light to be viewed directly through beam splitter mirror 20 and the viewing port 16.

The lamp carrier assembly 21 comprises a lamp 22 and a slit aperture 23 whose slot is aligned with the filament in the lamp 22, located in the lamp carrier 24. An electric contact 37 maintains electric contact with the lamp 22 and main sleeve 27 even while the lamp is rotated. A lens holder assembly 25 includes a lens holder 26 situated outside the lamp carrier sleeve 24. A main sleeve 27 whose distal end 28 is affixed to the head 15 is situated outside the lens holder 26. The main sleeve 27 has three vertical slots which engage the lens holder legs which hold the planet gears 36. This sleeve 27 has a longitudinal slot 29 which engages a not-shown protuberance on the doctor-side cover 15. This arrangement permits at 37 axial movement of the lens holder 26 relative to the main sleeve 27, but prohibits rotation of the lens holder 26. A wider-diameter shoulder portion 30 is situated at the proximal end of the main sleeve 27 and contains means, including a retaining ring 31, that holds the lamp carrier sleeve 24 within it to prevent axial movement, but permits the sleeve 24 to rotate freely.

The external control sleeve assembly 14 is formed of a top control sleeve 33 that is shouldered or stepped, and a generally cylindrical, internally-geared bottom control sleeve 34 that is fitted to it. These two portions define between them an annular gap 35 that captures the lens holder legs 37.

Figure 3:
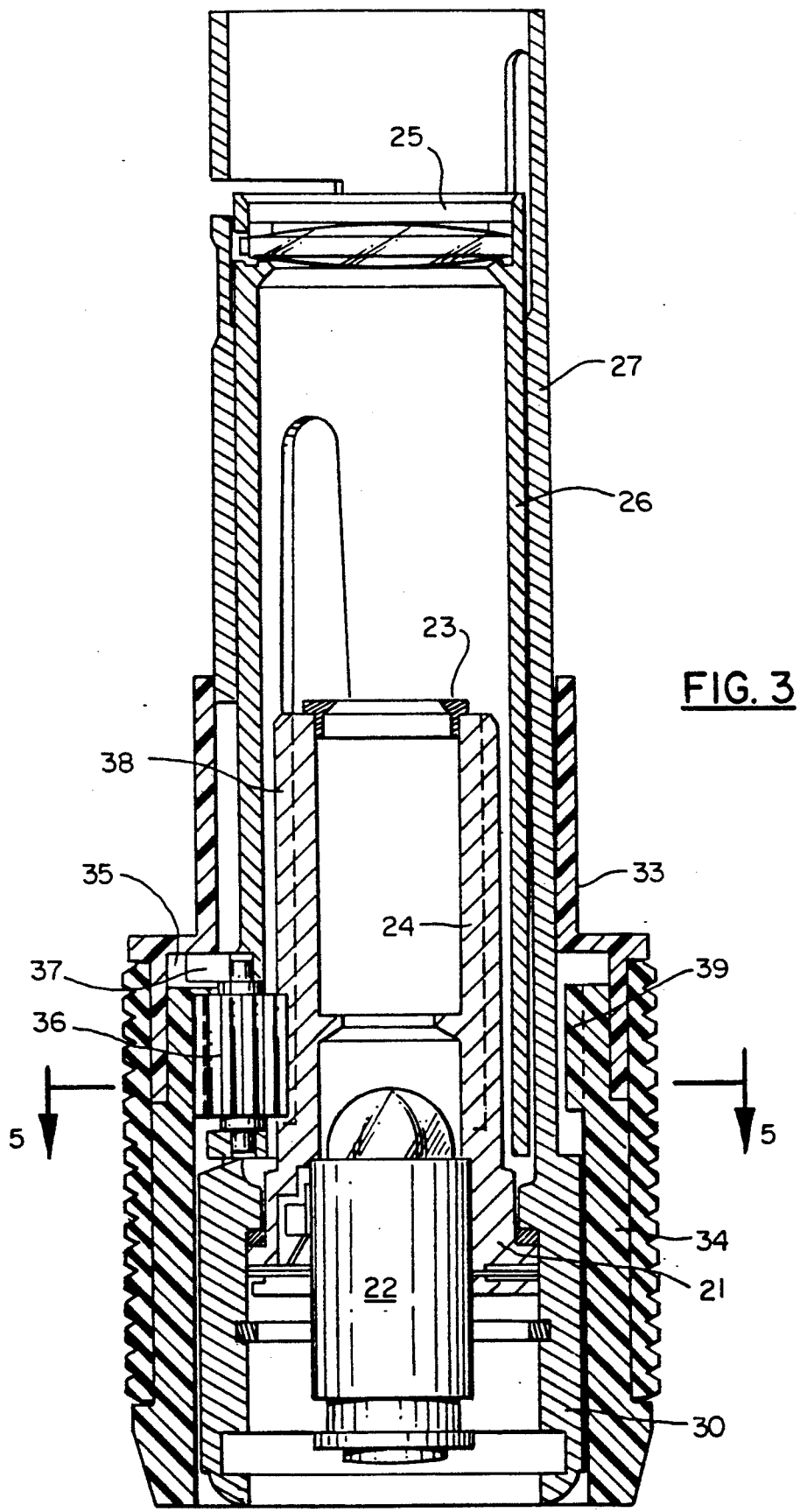
FIGS. 3 and 4 are cross-sectional views of the main sleeve subassembly showing divergent and convergent focus positions, respectively.
Figure 4:
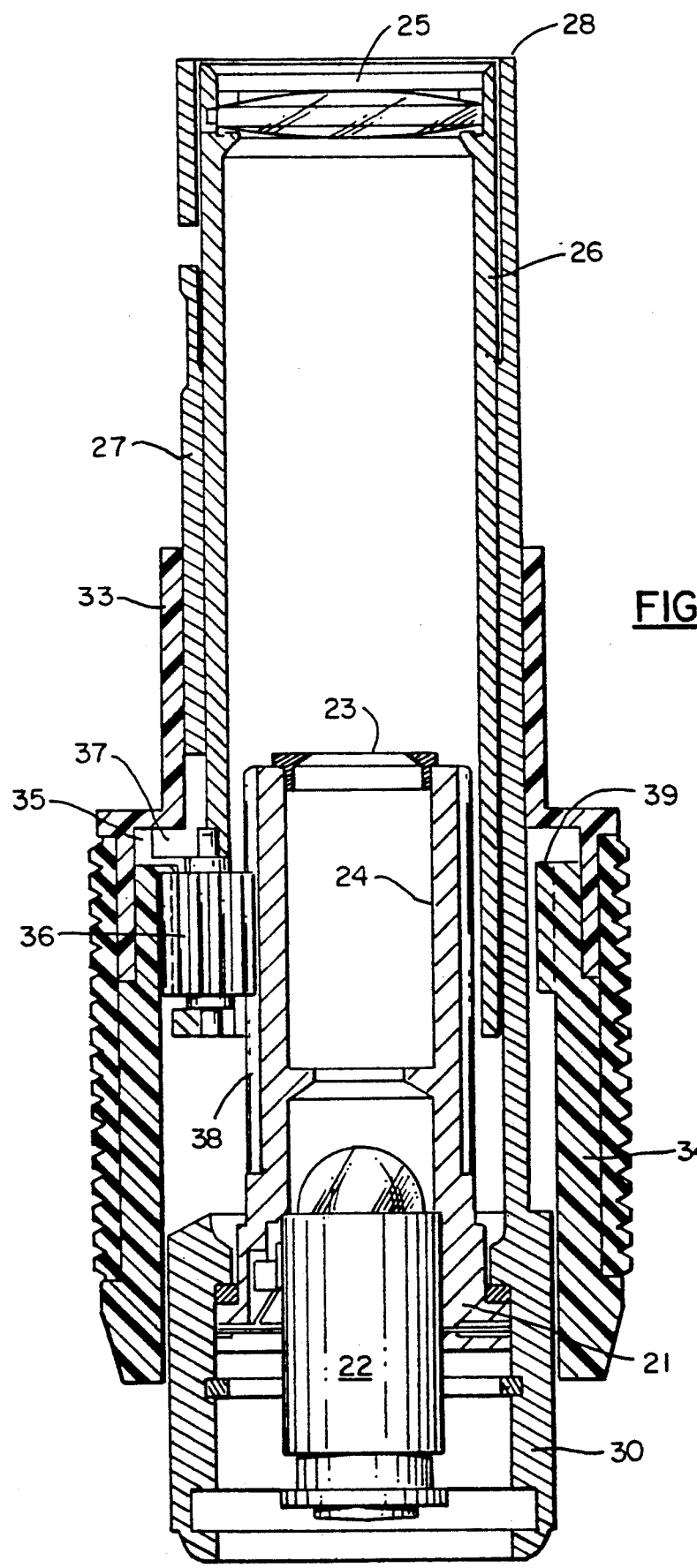

As shown in FIGS. 3–5, three planet gears 36 are disposed at 120 degree intervals and are carried on the legs 37 of the lens holder 26. The lamp carrier 24 has elongated teeth 38 formed on its outer surface, which engage with the teeth of the planet gears 36. On an inner surface of the bottom control sleeve 34, there are formed internal gear teeth 39 which also engage the planet gears 36.

Returning briefly to FIG. 1 and also FIG. 5, a cylindrical outer knurled grip surface 40 is situated around the control sleeve lower portion 34.

In a preferred embodiment, the planet gears 36 can favorably be formed of a tough plastic resin, including a synthetic lubricant filler. The lamp carrier sleeve 24 can favorably be formed of a heat resistant plastic resin and also including a synthetic lubricant chosen to withstand high temperatures which can be experienced with the halogen lamp, which is preferred for the lamp 22. The lower portion 34 of the control sleeve 14 is favorably formed of polymer which has favorable wear characteristics in this configuration. These materials are selected so that the planetary gear system will run with minimal friction and wear. Glass filled resin is chosen to withstand high temperatures which can be experienced with the halogen lamp, which is preferred for the lamp 22. The gear shape, as favorably shown in FIG. 5, is designed and intended for maximum recess action and smooth feel. With this arrangement, a quiet, smooth, and positive action is achieved.

The legs 37 of the lens holder 26, in addition to carrying the planet gears 36 also extend radially outward sufficiently to fit within the annular gap 35 formed in the control sleeve assembly 14. This axially constrains the lens holder 26 so that the latter will move in accordance with corresponding axial motion of the control sleeve. On the other hand, the planet gears 36 slide freely in the axial direction along the elongated sun gear teeth 38 formed in the lamp carrier 24. This permits the lens holder assembly 25 to be moved axially from a divergent ray position, as shown in FIG. 3, to a convergent ray position as shown in FIG. 4. The lens holder assembly 25 can be moved as appropriate to focus the projected streak or bar without change in the rotational disposition thereof.

Returning to FIG. 5, the planetary gear system including the bottom control sleeve 14, with the internal gear teeth 39, the planet gear 36, and the lamp carrier 24 with its sun gear teeth 38, rotates the lamp carrier assembly 21 corresponding to rotation of the control sleeve 14. As indicated in FIG. 5, the direction of rotation of the lamp 22 and slotted aperture 23 is reversed from that of the control sleeve 14. That is, clockwise rotation of the control sleeve 14 results in counterclockwise rotation of the lamp assembly, and vice versa.

With this control handle arrangement, the lamp 22 is carried at the proximal end of the control sleeve, preferably in direct contact with the power handle 11. Consequently, the lamp 22 is accessible can be removed and replaced without difficulty.

The lamp 22 rotates approximately twice for each rotation of the control sleeve. Thus, less sleeve motion is needed to rotate the streak.

While the retinoscope 10 is shown with a battery-type power handle 11, the present invention clearly also applies to retinoscopes having a cord type handles or those deriving their electrical power by other means.

While the invention has been described in detail with reference to a single preferred embodiment, it should be apparent that many modifications and variations would present themselves to those skilled in the art without departing from the scope and spirit of this invention, as defined in the appended claims.

What is claimed is:

1. Streak retinoscope which comprises a lamp assembly producing a transverse streak of light, and a control sleeve assembly effective to permit adjustment of focus of said streak of light and adjustment of its angular position as reflected by a beam splitter onto the retina of a patient's eye; said control sleeve assembly including a main sleeve having said head assembly mounted at its distal end; a lamp carrier sleeve within said main sleeve at its proximal end, said lamp carrier sleeve having said lamp assembly mounted therein, and having sun gear teeth extending axially on an outer surface, and said main sleeve including means holding said lamp carrier sleeve therewithin to permit angular rotation but prevent axial displacement, a lens holder sleeve disposed within said main sleeve over said lamp carrier sleeve and having a focussing lens assembly disposed at its distal end, including means holding the lens holder sleeve against rotation with respect to the main sleeve but permitting at least limited axial movement relative to said main sleeve, and including a plurality of planet gears carried at the proximal end of the lens holder sleeve and meshing with the sun gear teeth of said lamp carrier sleeve; and a control sleeve having an annular portion that extends entirely radially outward of the main sleeve said control sleeve being displacable axially and rotatable angularly, including means axially engaging a portion of said lens holder sleeve so that axial displacement of said control sleeve results in corresponding axial movement of the lens assembly for focusing said streak, without axial displacement of said lamp carrier sleeve and gear teeth formed on an inner surface of a portion of said control sleeve and meshing with said planet gears so that rotation of said control sleeve results in a corresponding angular rotation of said streak.

2. Streak retinoscope according to claim 1 wherein said lamp assembly includes a bar filament lamp carried at a proximal end of said lamp carrier sleeve.

3. Streak retinoscope according to claim 1 wherein said lens holder has at least one leg that projects radially out through a corresponding axial slot in said main sleeve, and said means of said control sleeve to engage the lens holder axially includes an annular recess formed in said control sleeve and into which said at least one leg projects.

4. Streak retinoscope according to claim 3 wherein said at least one leg serves also as a carrier for a respective one of said planet gears.

5. Streak retinoscope according to claim 1 wherein said control sleeve includes a knurled outer cylindrical surface to facilitate gripping of the control sleeve.

6. Streak retinoscope according to claim 1 wherein said main sleeve is of shouldered construction, with a wider diameter portion at its proximal end.

7. Streak retinoscope according to claim 1 wherein there are three of said planet gears carried at 120 degree intervals on said lens carrier sleeve.

8. Streak retinoscope according to claim 1 wherein said control sleeve and said planet gears are formed of respective synthetic resin materials.

9. Streak retinoscope according to claim 8 wherein said lamp carrier sleeve is formed of a synthetic resin material capable of withstanding high temperatures experienced with halogen lamp operation.

10. Streak retinoscope according to claim 1 wherein said lamp carrier rotates approximately twice for each rotation of the control sleeve.

11. Streak retinoscope which comprises a lamp assembly producing a transverse streak of light, and a control handle assembly effective to permit adjustment of focus of said streak of light and adjustment of its angular position as reflected by a beam splitter onto the retina of a patient's eye; said control handle assembly including a main sleeve having a head assembly mounted at its distal end; a lamp carrier sleeve generally within said main sleeve said lamp carrier sleeve having said lamp assembly mounted therein, and having gear teeth extending axially along an outer surface, and said main sleeve including means holding said lamp carrier sleeve therewithin to permit angular rotation but prevent axial displacement of said lamp carrier sleeve; a lens holder having a focusing lens assembly disposed at its distal end, including means holding the lens holder with respect to the main sleeve and permitting axial movement relative to the main sleeve, and a control sleeve disposed radially outward of the main sleeve and displaceable axially and freely rotatable angularly over 360 degrees, including means engaging a portion of said lens holder so that axial displacement of said control sleeve results in corresponding axial movement of the lens assembly for focussing said streak without axial movement of said lamp carrier sleeve, and interior gear teeth formed on an inner surface of said control sleeve, said interior gear teeth operatively engaging the gear teeth of the lamp carrier, so that rotation of said control sleeve results in a corresponding angular rotation of the streak.

* * * * *